US005803088A

United States Patent [19]

Blackwell

[11] Patent Number: 5,803,088

[45] Date of Patent: Sep. 8, 1998

[54] HEEL CUP FOR EXAMINATION TABLE

[76] Inventor: Linda Blackwell, 1025 N. Main St., Cedartown, Ga. 30125

[21] Appl. No.: 755,950

[22] Filed: Nov. 25, 1996

[51] Int. Cl.[6] .......... A61F 5/37

[52] U.S. Cl. .......... 128/882; 5/649

[58] Field of Search .......... 128/845, 846, 128/882, 892; 602/5, 36–40; 5/602, 624, 648, 649; 606/235–245

[56] References Cited

U.S. PATENT DOCUMENTS

| | | | |
|---|---|---|---|
| 3,355,163 | 11/1967 | Leinassar | 5/649 |
| 4,046,365 | 9/1977 | Dungan | 5/649 |
| 4,407,687 | 10/1983 | Mitchell | 5/649 |

*Primary Examiner*—Michael A. Brown

*Attorney, Agent, or Firm*—James B. Middleton

[57] ABSTRACT

A heel cup for a medical examination table has a solid bottom, and a heel receiving area that comfortably cradles the patient's heel. The rear portion to receive the heel is spherically shaped so the patient's heel can rotate as required and maintain the comfort of the patient. The forward portion that receives the extending foot of the patient is cylindrically shaped so the patient's foot will have a comfortable supporting surface regardless of the angle of the foot in the heel cup. A stub shaft extends from the rear of the heel cup for mounting the heel cup on the examination table. The stub shaft is positioned so that, when the heel cup is fixed to the table, the heel cup will be oriented as a mirror image of the patient's acetabulum. Thus, the patient's leg can move freely, rotating in the acetabulum at one end, and the heel cup at the other.

8 Claims, 1 Drawing Sheet

Fig. 1
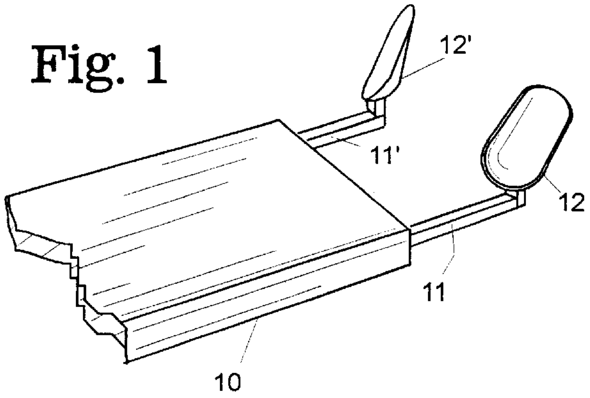
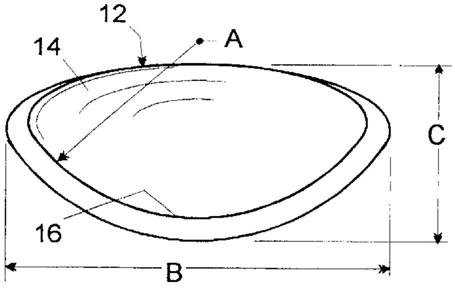
Fig. 2
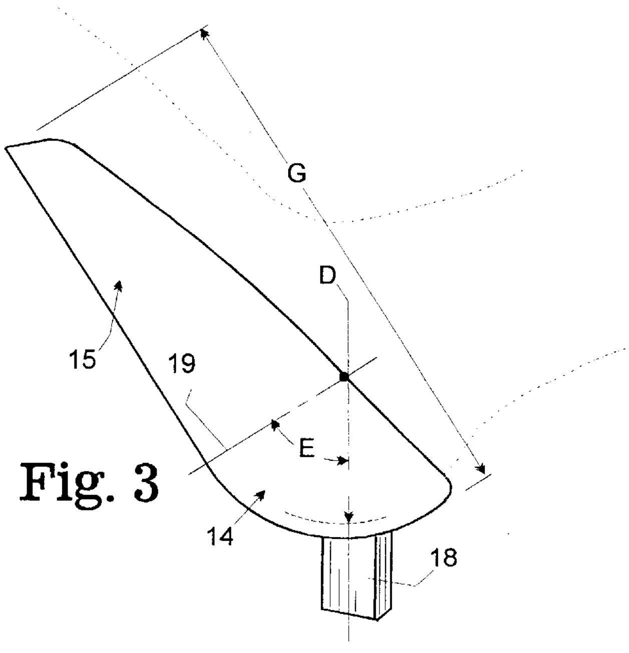
Fig. 3
Fig. 4
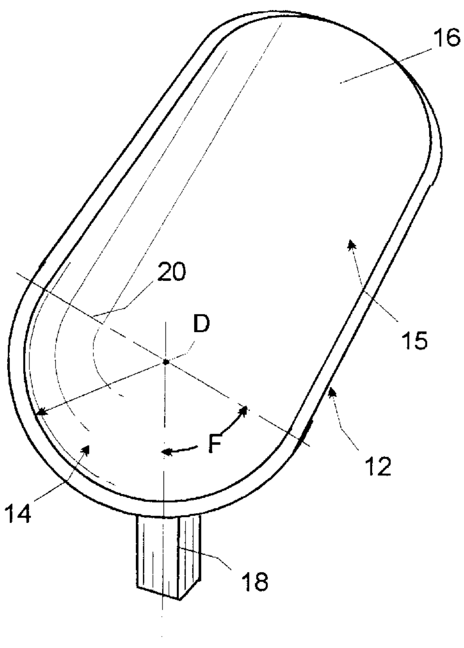

HEEL CUP FOR EXAMINATION TABLE

BACKGROUND OF THE INVENTION

1. Field of the Invention

This invention relates generally to foot rests, and is more particularly concerned with a heel cup for receiving the heel of a patient on an examination table or the like.

2. Discussion of the Prior Art

When a patient is on a medical examination table it is often, necessary or desirable for the patient's feet to be supported in stirrups or the like, with the knees bent, to allow easy access to the crotch area of the patient. Such a position is frequently required of women for the cervical examination, but men also require examinations in the crotch area.

The usual arrangement of an examination table is with the stirrups or the like supported from arms that extend from one end of the table. The patient's hips are then placed close to the end of the table, and the feet are supported by the stirrups. With the knees bent and separated, and the hips close to the end of the table, the doctor has reasonably easy access to the proper area of the patient.

The form of stirrup that has been used for many years comprises a heel cup, which receives only the heels of the patient. Supporting of the heels provides the greatest comfort, and lack of stress; but, the prior art heel cups have not been designed for comfort of the patient. The majority of heel cups now in use include a frame to surround the heel, and a single strap passing under the heel. Furthermore, the strap is usually straight, defining relatively sharp corners where the strap joins the frame. It will be understood that, as the patient holds his knees together or moves them apart, the heel rotates in the heel cup. Since the patient's heel tends to be rather rounded, and the heel cup is rather squared off, the heel cup tends to be uncomfortable. Even if the patient can find a comfortable position occasionally, rotation of the heel within the heel cup will usually be uncomfortable.

More recent heel cups have been made with a solid support for the heel rather than the single strap as discussed above. Such heel cups, however, have a completely flat bottom surface, and a wall at right angles to the bottom surface. As a result, the discomfort of the foot at various angles of rotation, and during the rotation itself, are continuing problems. Thus, the prior art has not provided a heel cup that comfortably supports a patient's foot and allows comfortable rotation to different angles as required by the doctor.

SUMMARY OF THE INVENTION

The present invention provides a heel cup for a medical examination table, the heel cup having a solid bottom surface that is curved generally to match the curvature of the lower surface of a person's heel. The bottom surface blends smoothly into the side walls of the heel cup so that, as a foot rotates, the heel will slide easily from one side, to the bottom, and to the other side of the heel cup without encountering sharp edges or corners. Further, the rear portion of the heel cup is generally spherical to cradle the rear of the heel, which tends to be somewhat spherical. The rear wall of the heel cup is high enough to give full support to the heel of the patient, while the spherical shape gives full comfort regardless of position.

The principle on which the shape of the heel cup is based is to shape the heel cup as a mirror image of the acetabulum, so the leg of the patient moves in the acetabulum on one end, and the heel cup on the other.

The heel cups of the present invention will have mounting means; and, in the preferred embodiment here presented, the mounting means comprise stub shafts receivable by an appropriate holder on the examination table. The mounting means may be placed to orient the heel cups properly for use.

BRIEF DESCRIPTION OF THE DRAWINGS

These and other features and advantages of the present invention will become apparent from consideration of the following specification when taken in conjunction with the accompanying drawings in which:

FIG. 1 is a perspective view showing one end of a medical examination table and having heel cups made in accordance with the present invention mounted thereon;

FIG. 2 is an elevational view of a heel cup shown in FIG. 1 as viewed from the distal end thereof;

FIG. 3 is a side elevational view thereof including the mounting means; and, FIG. 4 is a plan view thereof viewed from the heel receiving opening.

DETAILED DESCRIPTION OF THE EMBODIMENT

Referring now more particularly to the drawings, and to that embodiment of the invention here shown by way of illustration, FIG. 1 shows a portion of a medical examination table 10 having a pair of arms 11 and 11' extending therefrom. The arms 11 and 11' carry heel cups 12 and 12'. Those skilled in the art will understand that the general arrangement of the examining table 10 and the arms 11 and 11' with the heel cups 12 and 12' is known in the art, and the novel aspect shown in FIG. 1 of the drawings is the specific shape and orientation of the heel cups. Thus, the heel cups of the present invention may be used on any examination table, and that shown in FIG. 1 is by way of illustration only.

The purpose of the heel cups, from the standpoint of the physician, is to place the feet of the patient properly so the legs of the patient allow access to the patient's body as required. Many heel cups will accomplish this goal. When considering the patient, however, it should be understood that comfort is a very important aspect of the heel cups. A patient's feet are placed close to the body, or far from the body. A patient's feet will be rotated in the heel cups as the knees are placed together or separated. Heel cups therefore cannot be comfortable for the patient unless the heel cups are comfortable for all orientations of the feet. In spite of this fact, the prior art heel cups tend to require that the feet be in one position to achieve any measure of comfort, and some prior art heel cups are not comfortable in any position.

The present invention provides a heel cup, such as the heel cup 12, having a generally spherical rear portion 14, and a partially cylindrical forward portion 15. A person's heel has a somewhat spherical rear surface, so the heel will fit within the rear portion 14 as a ball and socket.

Those skilled in the art will understand that the head of the femur is received in the acetabulum, forming a ball-and-socket joint. The heel cup 12 is then formed as a mirror image of the acetabulum to receive the patient's heel. Thus, the patient's leg can move, and the two ends of the leg rotate easily in the heel cup and the acetabulum.

With attention directed to FIGS. 2, 3 and 4 of the drawings, it can be seen that the bottom surface 16 of the forward portion 15 is curved, the surface having a radius designated at A. If the bottom surface 16 were flat, as in prior art heel cups, the patient's foot would have no direct support when turned at an angle, which is to say there would be no supporting surface parallel to the bottom of the foot. With a shape as shown in FIG. 2, however, it will be seen that, as the foot rotates within the heel cup 12, there is always a portion of the curved bottom 16 that is parallel to the bottom of the foot. As a result, it will be understood that the curved bottom 16 provides initial comfort in that the foot is smoothly cradled, and provides continuing comfort in that the cradling of the foot remains reasonably consistent as the foot rotates with respect to the heel cup 12.

FIGS. 3 and 4 of the drawings show the rear, spherical, portion 14 of the heel cup 12. The radius of the spherical portion is indicated at D. Since the spherical portion 14 has a radius D, the width of the forward portion is approximately 2D. The total width of course diminishes as the side walls are lowered as shown in FIG. 3.

Those skilled in the art will understand that the precise dimensions of the heel cup 12 will vary, depending on the group of people for whom the heel cup is designed. Nevertheless, by way of example it has been determined that a heel cup for women may have a radius A of the forward portion 15 of about 1¾" or around 45 mm. The width B will be approximately the same as the diameter of the rear portion 14, or around 3" or 75 mm, so the interior radius D of the spherical rear portion will be about 30 mm. The height C in FIG. 2 may be about 1¼ or 30 mm. The overall length G may be around 3¾" or 95 mm.

The above stated dimensions will generally provide a heel cup suitable for women; but, for a heel cup for men, the dimensions should be increased by about ½", or around 15 mm.

As is shown in FIGS. 3 and 4, the heel cup 12 requires a mounting means for attachment to the arms 11 and 11' of the examination table 10. The mounting means here shown comprises a stub shaft 18 extending from the rear portion 14 of the heel cup 12. The shaft 18 is angled with respect to the heel cup 12 and the table arms 11 to provide the desired orientation of the heel cup 12. In view of the design principle of the heel cups it should be realized that the orientation will be a mirror image of the patient's acetabulum.

In the following discussion, directions rather arbitrarily assigned include the opening to receive the heel as the "top" of the heel cup, and the opposite is the "bottom". The rounded portion is the "rear" or "proximal" end, while the opposite is the "front" or "distal" end. These designations are for convenience only and have no bearing on the actual orientation of the heel cup with respect to the table, the floor, or the patient.

Looking at FIG. 3 of the drawings, the shaft 18 is angled downwardly. A centerline of the spherical portion 14 is shown at 19; and, the shaft 18 is directed along a line at angle E from the centerline 19. The angle E may be around 60°, though of course this angle may vary depending on the structure of the arms 11 and 11' on the table 10. Looking at FIG. 4, the shaft 18 is disposed at an angle from the heel cup 12. In FIG. 4 a lateral diameter 20 of the spherical portion 14 is shown, and the shaft 18 is disposed at an angle F from the diameter 20. Again, this angle may be varied considerably depending on the structure of the arms 11 and 11'.

It can be seen in both FIG. 3 and FIG. 4 that the stub shaft 18 is rectangular, and its sides are not parallel to the plane of the top of the heel cup 12. Rather, the sides of the shaft 18 will be disposed parallel to the sides of the table 10, and the heel cups 12 and 12' will be disposed at the correct angle as discussed above, to orient the heel cup as a mirror image of the acetabulum. The precise position of the shaft 18 will therefore be determined based on the configuration of the arms 11 and 11'.

From the foregoing it will be recognized that the heel cup of the present invention provides comfort for a patient regardless of the position of the patient. Even as the patient must change leg position and rotate his or her foot in the heel cups, the heel cup 12 will continue to provide both comfortable support for the heel and easy motion of the leg.

It will of course be understood by those skilled in the art that the particular embodiment of the invention here presented is by way of illustration only, and is meant to be in no way restrictive; therefore, numerous changes and modifications may be made, and the full use of equivalents resorted to, without departing from the spirit or scope of the invention as outlined in the appended claims.

I claim:

1. A heel cup for a medical examination table, said heel cup supporting a heel of a patient who is lying on said medical examination table, said patient having at least one leg including said heel, and an acetabulum for receiving an end of a bone in said leg, said heel cup comprising a spherically shaped rear portion, the rear end of said heel cup being circular in top plan view and circular in side elevational view for cradling the heel, and a cylindrically shaped forward portion, said rear portion and forward portion being integrally formed, said rear portion being sized to receive the heel of the patient while the foot of the patient extends into said forward portion, said heel cup being oriented with respect to the patient as a minor image of said acetabulum.

2. A heel cup as claimed in claim 1, wherein said cylindrically shaped forward portion has a radius such that, as the foot of the patient rotates within said heel cup, a line parallel to the bottom of the foot will be tangent to said cylindrically shaped forward portion.

3. A heel cup as claimed in claim 1, said heel cup further including mounting means for mounting said heel cup on said examination table.

4. A heel cup as claimed in claim 3, said mounting means comprising a shaft extending from said rear portion of said heel cup.

5. A heel cup as claimed in claim 4, wherein said medical examination table further includes a second heel cup for supporting a second heel of a patient, said second heel cup including a shaft extending therefrom as supporting means.

6. A heel cup as claimed in claim 1, wherein said spherically shaped rear portion has a radius in the range of 30 to 45 mm, and said cylindrically shaped forward portion has a radius in the range of 45 to 60 mm.

7. A heel cup as claimed in claim 6, wherein said heel cup has an overall length in the range of 95 to 110 mm.

8. A heel cup as claimed in claim 7, wherein said radius of said rear portion is about 30 mm, the radius of said forward portion is about 45 mm., said length is about 95 mm, and said heel cup has a height of about 30 mm.

* * * * *

UNITED STATES PATENT AND TRADEMARK OFFICE

CERTIFICATE OF CORRECTION

PATENT NO. : 5,803,088

DATED : September 8, 1998

INVENTOR(S) : Linda Blackwell

It is certified that error appears in the above-identified patent and that said Letters Patent is hereby corrected as shown below:

Claim 1, line 35, change "minor" to --mirror--.

Signed and Sealed this

Twenty-second Day of December, 1998

Attest:

BRUCE LEHMAN

Attesting Officer

*Commissioner of Patents and Trademarks*